United States Patent
Majeed et al.

(10) Patent No.: US 10,864,154 B2
(45) Date of Patent: Dec. 15, 2020

(54) SKIN CARE COMPOSITIONS AND THEIR APPLICATIONS

(71) Applicants: Muhammed Majeed, Bangalore (IN); Kalyanam Nagabhushanam, East Windsor, NJ (US); Lakshmi Mundkur, Bangalore (IN)

(72) Inventors: Muhammed Majeed, Bangalore (IN); Kalyanam Nagabhushanam, East Windsor, NJ (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/372,663

(22) Filed: Apr. 2, 2019

(65) Prior Publication Data
US 2019/0298641 A1  Oct. 3, 2019

(51) Int. Cl.
*A61K 8/67* (2006.01)
*A61Q 19/08* (2006.01)
*A61K 8/39* (2006.01)

(52) U.S. Cl.
CPC ............... *A61K 8/676* (2013.01); *A61K 8/39* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 8,580,317 | B2 * | 11/2013 | Waugh | A61K 31/192 424/725 |
| 2003/0134264 | A1 * | 7/2003 | Maeda | A61K 8/492 435/4 |
| 2006/0216252 | A1 * | 9/2006 | Baschong | A61P 17/16 424/62 |
| 2006/0263309 | A1 * | 11/2006 | Bissett | A61K 8/675 424/59 |
| 2011/0091398 | A1 * | 4/2011 | Majeed | A61P 43/00 424/59 |
| 2015/0209243 | A1 * | 7/2015 | Shiroya | A61K 8/02 424/401 |
| 2016/0089310 | A1 * | 3/2016 | Brock | A61K 8/0279 424/401 |

OTHER PUBLICATIONS

Hsu., New multi-functional and stable vitamin C for skin lightening, NutraCos Cosmetic, May/Aug. 2012, p. 1, 6-7 (Year: 2012).*
Branna., Preservative Update, https://www.happi.com/contents/view_features/2006-05-19/preservative-update-85041/, May 19, 2006 (Year: 2006).*
Merriam-Webster, Definition of Melanogenesis, https://www.merriam-webster.com/dictionary/melanogenesis, retrieved online May 11, 2020 (Year: 2020).*
Corum, Corum 9515, http://www.corum.com.tw/tw/products_more.php?c=4&v=9&d=15, retrieved online May 12, 2020 (Year: 2020).*

* cited by examiner

*Primary Examiner* — Jennifer A Berrios

(57) ABSTRACT

The present invention discloses a synergistic composition comprising 3-O-ethyl-ascorbic acid and tetrahydrocurcuminoids for use as a skin lightening agent. The invention also discloses a method of inhibiting melanin biosynthesis and tyrosinase activity in mammalian skin cells using a composition comprising 3-O-ethyl-ascorbic acid and tetrahydrocurcuminoids.

12 Claims, No Drawings

SKIN CARE COMPOSITIONS AND THEIR APPLICATIONS

CROSS-REFERENCE TO RELATED APPLICATIONS

This is a conventional application claiming priority to Indian Provisional Application No. IN 201841012637 filed on 3 Apr. 2018.

FIELD OF INVENTION

The present invention relates to novel skin care compositions. More specifically, the invention relates to skin lightening compositions comprising alkyl ascorbic acid.

BACKGROUND OF THE INVENTION

Description of Prior Art

Hyperpigmentation is a condition wherein patches of skin darken due to the overproduction of melanin. It is caused due a variety of reasons which include age, skin conditions such as acne, injuries to the skin, surgeries etc. Age spots and hyperpigmentation are also caused due to over exposure of the harmful UV-A. UV-B radiation from the sun. This causes excess production of melanin which acts as a shield against this harmful radiation, resulting in skin tanning and dark spots.

Most of the treatment methods include administration of creams, lotions containing actives which inhibit melanin production. Creams containing hydroquinones and cortisone are widely used as skin lightening agents. Alkyl-ascorbic acid is now currently being used is most of the cosmetic formulations owing to its greater stability and anti-oxidant property. It is also a known skin lightening agent. The following prior art documents disclose the use of alkyl-ascorbic acid, specifically ethyl-ascorbic acid of use as a skin care agent 1. U.S. Pat. No. 6,861,050 discloses a composition comprising polymerization inhibitor of a biological dihydroxyindole compound and 3-O-ethyl ascorbic acid for preventing darkening of the skin or inhibiting melanization caused by the irradiation.
2. US patent application no. 20120189564 discloses compositions comprising Portulaca extract and a vitamin C derivative selected from ascorbyl glucoside (ASG), magnesium ascorbyl phosphate and ethyl ascorbic acid for inhibiting melanin formation.
3. WO/2016/163023 discloses a composition comprising 45-49 wt % ethyoxydiglycol, 21-25 wt % propylene glycol, 13-17 wt % ascorbic acid, 3-7 wt % 3-O-ethyl-ascorbic acid for skin whitening.

It is evident from the above prior art documents that ethyl-ascorbic acid is widely being used in combination with other ingredients for melanin inhibition and skin whitening effect. However, most of the ingredients used along with 3-O-ethyl-ascorbic acid are synthetic in origin and produce side effects such as skin rashes and irritation. A safe, effective and natural alternative is warranted which can be combined with 3-O-ethyl-ascorbic acid for inhibiting melanin and for use as a skin lightening agent.

Botanical extracts have been reported to exhibit skin lightening effects (Zhu and Gao, The Use of Botanical Extracts as Topical Skin-Lightening Agents for the Improvement of Skin Pigmentation Disorders, Journal of Investigative Dermatology Symposium Proceedings 2008; 13:20-24, doi:10.1038/jidsyminp.2008.8). Japanese patent JPH0782134, also discloses a cosmetic composition for preventing damage due to ultraviolet rays comprising L-3-O-ethyl-ascorbic acid and natural molecule kojic acid. However, a safe and effective alternative natural ingredient for use as a skin lightening agent along with ethyl ascorbic acid is warranted. Curcuminoids from *Curcuma longa* are known to inhibit tyrosinase enzyme and melanin production (Tu et al., Curcumin inhibits melanogenesis in human melanocytes, Phytother Res. 2012; 26(2):174-9). The skin lightening effect of another ingredient from *Curcuma longa*, tetrahydrocurcuminoids in combination with ethyl-ascorbic acid is not evaluated yet. The present invention discloses a synergistic composition comprising ethyl-ascorbic acid and tetrahydrocurcuminoids for inhibiting melanin production and tyrosinase inhibition.

The principal object of the invention is to disclose a composition comprising alkyl-ascorbic acid and tetrahydrocurcuminoids for use as a skin lightening agent.

It is another object of the invention is to disclose a method for inhibiting melanin production using a composition comprising alkyl-ascorbic acid and tetrahydrocurcuminoids.

It is yet another object of the invention is to disclose a method for inhibiting the activity of enzyme tyrosinase using a composition comprising alkyl-ascorbic acid and tetrahydrocurcuminoids.

The present invention solves the above mentioned objectives and provides further related advantages.

SUMMARY OF THE INVENTION

The present invention discloses a synergistic composition comprising 3-O-ethyl-ascorbic acid and tetrahydrocurcuminoids for use as a skin lightening agent.

The invention also discloses a method of inhibiting melanin biosynthesis in mammalian skin cells using a composition comprising 3-O-ethyl-ascorbic acid and tetrahydrocurcuminoids.

Further, a method of inhibiting the activity of enzyme tyrosinase in mammalian skin cells using a composition comprising 3-O-ethyl-ascorbic acid and tetrahydrocurcuminoids, is also disclosed.

Other features and advantages of the present invention will become apparent from the following more detailed description, which illustrate, by way of example, the principle of the invention.

DESCRIPTION OF PREFERRED EMBODIMENTS

In a preferred embodiment, the invention discloses a cosmetic composition comprising 3-O-alkyl-ascorbic acid and tetrahydrocurcuminoids. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 1-4% w/w and 0.1-2% w/w respectively. In another related aspect, the compositions further includes diluents, chelating agents, thickeners, humectants, emulsifiers, emollients, anti-oxidants, solubilizers, and other cosmeceutically accepted excipients. In another related aspect, the composition is used as a skin lightening agent by inhibiting melanogenesis and tyrosinase activity.

In another preferred embodiment, the invention discloses a method of inhibiting melanogenesis in mammalian skin cells, comprising step of bringing into contact skin cells with a composition comprising 3-O-alkyl-ascorbic acid and tetrahydrocurcuminoids, to bring about a reduction in melanin synthesis. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 0.5-500 µg/ml and 3-100 µg/ml respectively. In another related aspect, the 3-O-alkyl-ascorbic acid and tetrahydrocurcuminoids are present in the doses of 1-4% w/w and 0.1-2% w/w respectively in the composition. In another related aspect, the compositions further includes diluents, chelating agents, thickeners, humectants, emulsifiers, emollients, anti-oxidants, solubilizers, and other cosmeceutically accepted excipients. In another related aspect, the mammalian skin cells are preferably melanocytes. In another related aspect, the mammal is human.

In another preferred embodiment, the invention discloses a method of inhibiting tyrosinase activity in mammalian skin cells, comprising step of bringing into contact skin cells with a composition comprising 3-O-alkyl-ascorbic acid and tetrahydrocurcuminoids, to bring about an inhibition of tyrosinase activity. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 0.5-500 g/ml and 3-100 µg/ml respectively. In another related aspect, the 3-O-alkyl-ascorbic acid and tetrahydrocurcuminoids are present in the doses of 1-4% w/w and 0.1-2% w/w respectively in the composition. In another related aspect, the compositions further includes diluents, chelating agents, thickeners, humectants, emulsifiers, emollients, anti-oxidants, solubilizers, and other cosmeceutically accepted excipients. In another related aspect, the mammalian skin cells are preferably melanocytes. In another related aspect, the mammal is human.

In another related aspect, the invention discloses a composition comprising 3-O-alkyl-ascorbic acid and tetrahydrocurcuminoids for use in inhibiting melanin synthesis. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 0.5-500 µg/ml and 3-100 µg/ml respectively. In another related aspect, the 3-O-alkyl-ascorbic acid and tetrahydrocurcuminoids are present in the doses of 1-4% w/w and 0.1-2% w/w respectively in the composition. In another related aspect, the compositions further includes diluents, chelating agents, thickeners, humectants, emulsifiers, emollients, anti-oxidants, solubilizers, and other cosmeceutically accepted excipients. In another related aspect, the mammalian skin cells are preferably melanocytes. In another related aspect, the mammal is human.

In another preferred embodiment, the invention discloses a composition comprising 3-O-alkyl-ascorbic acid and tetrahydrocurcuminoids for use in inhibiting tyrosinase activity in mammalian skin cells. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 0.5-500 µg/ml and 3-100 µg/ml respectively. In another related aspect, the 3-O-alkyl-ascorbic acid and tetrahydrocurcuminoids are present in the doses of 1-4% w/w and 0.1-2% w/w respectively in the composition. In another related aspect, the compositions further includes diluents, chelating agents, thickeners, humectants, emulsifiers, emollients, anti-oxidants, solubilizers, and other cosmeceutically accepted excipients. In another related aspect, the mammalian skin cells are preferably melanocytes. In another related aspect, the mammal is human.

In another preferred embodiment, the invention discloses a composition comprising 3-O-alkyl-ascorbic acid and tetrahydrocurcuminoids for use as a skin lightening agent. In a related aspect, the 3-O-alkyl-ascorbic acid is preferably 3-O-ethyl-ascorbic acid. In another related aspect, the tetrahydrocurcuminoids comprises of tetrahydrocurcumin, tetrahydrodemethoxycurcumin, tetrahydrobis-demethoxycurcumin. In another related aspect, the tetrahydrocurcuminoids comprises of tetrahydrocurcumin and tetrahydrodemethoxycurcumin. In another related aspect, the tetrahydrocurcuminoids is preferably greater than 95% w/w tetrahydrocurcumin. In another related aspect, the 3-O-alkyl-ascorbic acid and tetrahydrocurcuminoids are present in the concentrations of 0.5-500 µg/ml and 3-100 µg/ml respectively. In another related aspect, the 3-O-alkyl-ascorbic acid and tetrahydrocurcuminoids are present in the doses of 1-4% w/w and 0.1-2% w/w respectively in the composition. In another related aspect, the compositions further includes diluents, chelating agents, thickeners, humectants, emulsifiers, emollients, anti-oxidants, solubilizers, and other cosmeceutically accepted excipients.

Specific illustrative examples enunciating the most preferred embodiments are included herein below.

EXAMPLES

Example 1: Tyrosinase Inhibition

Background

The color of human skin is determined by the synthesis and distribution of melanin pigment. Melanin synthesis is catalyzed by Tyrosinase—a rate limiting copper containing enzyme (Sigma, monophenol oxygenase, EC1.14.18. 1).

Compounds that inhibit the formation of melanin pigment by inhibiting Tyrosinase activity have been used to prevent skin pigmentation. Tyrosinase catalyses three different reactions in melanin's biosynthetic pathway, which include the hydroxylation of tyrosine to 3,4-dihydroxyphenylalanine (DOPA), the oxidation of DOPA to DOPA quinone; and the oxidation of 5,6-dihydroxyindole (DHI) to indole-quinone. The first of these reactions in the synthesis of melanin is the most biologically critical, since the rest of the reaction sequence can proceed spontaneously at physiological conditions.

Principle:

Tyrosinase catalyses three different reactions in melanin biosynthetic pathway. The hydroxylation of tyrosine to 3,4-dihydroxyphenylalanine (DOPA), The oxidation of DOPA to DOPA quinone; and the oxidation of 5,6-dihydroxyindole (DHI) to indole-quinone. The first of these reactions in the synthesis of melanin is the most biologically critical, since the rest of the reaction sequence can proceed spontaneously at a physiological pH.

Tyrosinase acts on L-Tyrosine forming a pink colored complex, the intensity of which is measured at 492 nm. The Tyrosinase activity in the presence and absence of inhibitor is assayed spectrophotometrically at 492 nm using a Microplate reader.

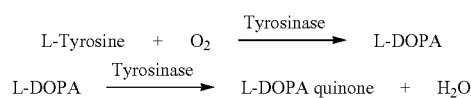

Methodology:
Materials

| Product | Source | Storage |
|---|---|---|
| Mushroom Tyrosinase | Sigma | −20° C. |
| L-Tyrosine Disodium salt | Sigma | 2-8° C. |
| Disodiumhydrogen phosphate | Merck | RT |
| Sodiumdihydrogen phosphate | Fischer sci | RT |
| Dimethyl sulfoxide (DMSO) | Sigma | RT |

Reagent Preparation

Phosphate Buffer, 0.25 mM (pH 6.5):

Sodium phosphate buffers was prepared by dissolving 1.4196 g of Disodium hydrogen phosphate (A) and 1.5601 g of Sodium dihydrogen phosphate dehydrate (B) in 100 ml of double distilled water individually. 68.5 ml of Solution A and 31.5 ml of Solution B were mixed, volume made up to 400 ml and pH adjusted to 6.5 using 0.1N HCL or 0.1N NaOH.

Mushroom Tyrosinase Enzyme:

Mushroom Tyrosinase enzyme is prepared by dissolving entire content in 0.05 mM, pH 6.5 pre-chilled enzyme buffer to get 5000 U/ml. Gentle shaking for five minutes aids in dissolution of enzyme. Aliquot the stock into vials of 100 µl each and keep at −80° until use for at least 2 months. Multiple freeze-thaw cycles of the enzyme must be avoided.

L-Tyrosine Sodium Salt (2.53 Mm):

A stock of 2.50 mM L-Tyrosine Disodium salt (Sigma) is prepared in 1.5 mM phosphate buffer (pH 6.5) by dissolving 2.845 mg/5 ml.

Preparation of Samples:

Samples were dissolved in DMSO and further dilutions were carried out in buffer

Assay Method

The assay was performed in a 96 well clear microtitre plate. Different concentrations of the composition comprising ethyl-ascorbic acid and tetrahydrocurcuminoids were pre incubated with 10 µl of 6000 U/ml stock Solution of Mushroom Tyrosinase (f.c. 6 U/well) at 37° C. for 10 minutes. The reaction is initiated by adding 2.5 mM L-Tyrosine disodium and the absorbance is read immediately every minute until 15 minutes using the microplate reader at 492 nm. A test blank well was prepared for each sample without the enzyme. Enzyme reaction with vehicle alone served as a control for enzyme activity. Kojic acid was used as a positive control.

Calculation:

The results are expressed as $IC_{50}$ values using Graphpad prism software. The percentage of inhibition of melanin is calculated as follows, $$\% \text{ Inhibition} = \frac{C - T}{C} \times 100$$

Where C-absorbance in control and T-absorbance in test sample

Results

The results of the tyrosinase inhibition assay was tabulated in Table 1:

TABLE 1

| Inhibition of tyrosinase activity by ethyl-ascorbic acid and tetrahydrocurcuminoids | | | | | | |
|---|---|---|---|---|---|---|
| Ethyl-ascorbic acid (EAA) | | Tetrahydrocurcuminoids (THC) | | Ethyl-ascorbic acid (EAA) + Tetrahydrocurcuminoids (THC) | | |
| Concentration (µg/ml) | % Inhibition | Concentration (µg/ml) | % Inhibition | Concentration (µg/ml) EAA / THC | % Inhibition | Enhancement in activity |
| 500 | 28.266 | 90 | 34.08 | 500.0 / 90 | 76.14 | 18.12 |
| 250 | 11.558 | 45 | 22.56 | 250.0 / 45 | 58.24 | 41.42 |
| 125 | Nil | 22.5 | 16.8 | 125.0 / 22.5 | 37.78 | 55.53 |
| 62.5 | Nil | 11.25 | 13.92 | 62.5 / 11.25 | 21.59 | 35.53 |

The results indicated that combination of tetrahydrocurcuminoids and ethyl-ascorbic acid resulted in a synergistic increase in anti Tyrosinase activity, with maximum activity at about 22.5 µg/ml and 125 µg/ml respectively.

Example 2: Melanogenesis Inhibition Activity

Background:

Melanin pigments are produced by melanocytes in the basal layer of the epidermis which subsequently transfer it to keratinocytes for distribution in the upper layer of the skin epidermis. Melanin determines the skin color and also plays an important role preventing skin damage. B16 F1 are mouse melanoma cells which produce melanin when stimulated with melanocyte stimulating hormone (c-MSH) in vitro in cell culture.

Principle:

The intracellular melanin in B16F1 mouse melanoma cells is extracted by 1N NaOH. The brown colored melanin thus extracted is estimated at 405 nm. The synthesis of melanin is inhibited in the presence of inhibitor which results in reduced absorbance at 405 nm.

Methodology:

Materials

| Reagents | Source | Storage |
| --- | --- | --- |
| Dulbecco's Minimal Essential medium | Gibco | 4-8° C. |
| Phosphate Buffered Saline | Sigma | RT |
| Trypsin | Sigma | −20° C. |
| Fetal Bovine Serum | Gibco | −20° C. |
| Gentamycin | HiMedia | −20° C. |
| Glacial acetic acid | Fisher | RT |
| Dimethylsulphoxide | Sigma | RT |
| Sodium bicarbonate | Fischer | RT |
| NaOH | Fischer | RT |
| HCl | Merck | RT |
| Melanocyte stimulating hormone | Sigma | RT |

Reagent Preparation

DMEM Media:

All activities were performed inside the Biological safety cabinet (BSC). The contents of one packet were dissolved into 1 L of sterile double distilled water, and 3.7 g of Sodium bicarbonate was added to get a pH of 7.2-7.6. The solution was filtered using membrane filtration unit. Gentamycinn 40 µg/ml) and (Fetal Bovine Serum at a final concentration of 10% was added to the filtered media and stored at 4° C.

PBS (pH 7.2±0.5):

One PBS tablet was dissolved in 200 ml of double distilled water to obtain a 137 mM NaCl, 2.7 mM KCl and 10 mM phosphate buffer solution (pH 7.4 at 25° C.) and sterilize by autoclaving and stored at 4° C.

1 nM MSH:

MSH Stock was prepared at 1 mg/ml in distilled water. MSH at a final concentration of 1 nM was used to stimulate melanogenesis Assay Method B16F1 mouse melanoma cells were cultured for 24 hours in a 96 well microtiter plate at a seeding density of 5000 cells per well. Cells are treated with varying non cytotoxic concentrations of the sample over a period of 72 hours along with melanin stimulating hormone ($\alpha$-MSH) to induce the synthesis of melanin pigment. Untreated cells and cells without $\alpha$-MSH addition were used as positive and negative control. The melanin produced by the cells was extracted by 1N NaOH and the absorbance was read at 405 nm in a Microplate reader. The inhibitory effect of the sample is calculated based on the degree of inhibition of melanin formation.

Calculation:

The results are expressed as $IC_{50}$ values using Graph pad prism software. The percentage of inhibition of melanin is calculated as follows, $$\% \text{ Inhibition} = \frac{C - T}{C} \times 100$$

Where C-absorbance due to melanin in untreated cells

T-absorbance due to melanin in sample treated cells

Results

The results are tabulated as table 2:

TABLE 2

Melanogenesis inhibition potential of ethyl-ascorbic acid and tetrahydrocurcuminoids composition

| Ethyl-ascorbic acid (EAA) | | Tetrahydrocurcuminoids (THC) | | Ethyl-ascorbic acid (EAA) + Tetrahydrocurcuminoids (THC) | | | |
| --- | --- | --- | --- | --- | --- | --- | --- |
| | | | | Concentration (µg/ml) | | | Enhancement |
| Concentration (µg/ml) | % Inhibition | Concentration (µg/ml) | % Inhibition | EAA | THC | % Inhibition | in activity |
| 1.25 | Nil | 6.25 | 8.72 | 1.25 | 6.25 | 11.36 | 23.23944 |
| 0.625 | Nil | 3.125 | Nil | 0.625 | 3.125 | 11.63 | 100% |

Combination of tetrahydrocurcuminoids and ethyl-ascorbic acid resulted in a synergistic inhibition of melananogenesis. While tetrahydrocurcuminoids and ethyl-ascorbic acid did not show any melanogenesis inhibition at 0.625 ad 3.125 µg/ml respectively. The combination of tetrahydrocurcuminoids and ethyl-ascorbic acid at the same concentration showed an 11.63% inhibition which is an unexpected finding.

Example 3: Formulation Comprising Ethyl-Ascorbic Acid and Tetrahydrocurcuminoids The composition comprising ethyl-ascorbic acid and tetrahydrocurcuminoids was formulated with diluents, chelating agents, thickeners, humectants, emulsifiers, emollients, anti-oxidants, solubilizers, and other cosmeceutically accepted excipients. Table 3 provides an illustrative example of a formulation comprising ethyl-ascorbic acid and tetrahydrocurcuminoids

TABLE 3

Formulation comprising ethyl-ascorbic acid and tetrahydrocurcuminoids

| Phase | Ingredients | Functions |
|---|---|---|
| A | Purified Water | Diluent |
|  | Disodium EDTA | Chelating Agent |
|  | Biopol Crystals | Thickener |
|  | Glycerin | Humectant |
| B | Olivem 1000 | Emulsifier |
|  | DUB CO | Emollient |
|  | GMS SE | Emulsifier |
|  | Cetyl Alcohol | Emollient |
|  | Shea Butter | Emollient |
|  | Imex IN3 | Emollient |
|  | Tinogard TT | Anti Oxidant |
|  | Tinogard TS | Anti Oxidant |
| C | Tween 20 | Solubilizer |
|  | Tetrahydrocurcuminoids | Skin Lightening/Whitening |
| D | Purified Water | Diluent |
|  | 3-O-Ethyl-Ascorbic Acid | Skin Lightening/Whitening |
| E | Euxyl PE 9010 | Preservative |
|  | Xiameter PMX 3031 | Detackification |
| F | Purified Water | Diluent |
|  | Sodium Metabisulfite | Anti Oxidant |

The above formulation is merely an example, any formulation containing the above active ingredient intended for the said purpose will be considered equivalent.

The above formulation was tested for its melanogenesis and tyrosinase inhibition potential. The results are tabulated in table 4.

TABLE 4

Melanogenesis and tyrosinase inhibition potential of formulation comprising ethyl-ascorbic acid and tetrahydrocurcuminoids

| Concentration (µg/ml) 2% EAA + 0.25% THC | % Inhibition |
|---|---|
| Tyrosinase Inhibition Activity | |
| 1000 | 11.86 |
| 100 | 6.31 |
| 10 | 0.37 |
| Melanogenesis Inhibition Activity | |
| 100 | 17.45 |

The results indicated that the formulation showed good tyrosinase and melanogenesis inhibition activity and can be used as a skin lightening agent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A method of inhibiting melanogenesis in mammalian skin cells, comprising a step of bringing into contact skin cells with a composition essentially consisting of 3-O-ethyl-ascorbic acid and tetrahydrocurcuminoids, to bring about a reduction in melanin synthesis, wherein the 3-O-ethyl-ascorbic acid and tetrahydrocurcuminoids are present in the concentrations of 0.5-500 µg/ml and 3-100 µg/ml respectively.

2. The method as in claim 1, wherein the tetrahydrocurcuminoids comprises of tetrahydrocurcumin, tetrahydrodemethoxycurcumin, tetrahydrobisdemethoxycurcumin.

3. The method as in claim 1, wherein the tetrahydrocurcuminoids comprises of tetrahydrocurcumin and tetrahydrodemethoxycurcumin.

4. The method as in claim 1, wherein the tetrahydrocurcuminoids is greater than 95% w/w tetrahydrocurcumin.

5. The method as in claim 1, wherein the mammalian skin cells are melanocytes.

6. The method as in claim 1, wherein the mammal is human.

7. A method of inhibiting tyrosinase activity in mammalian skin cells, comprising a step of bringing into contact skin cells with a composition essentially consisting of 3-O-ethyl-ascorbic acid and tetrahydrocurcuminoids, to bring about a reduction in melanin synthesis, wherein the 3-O-ethyl-ascorbic acid and tetrahydrocurcuminoids are present in the concentrations of 0.5-500 µg/ml and 3-100 µg/ml respectively.

8. The method as in claim 7, wherein the tetrahydrocurcuminoids comprises of tetrahydrocurcumin, tetrahydrodemethoxycurcumin, tetrahydrobisdemethoxycurcumin.

9. The method as in claim 7, wherein the tetrahydrocurcuminoids comprises of tetrahydrocurcumin and tetrahydrodemethoxycurcumin.

10. The method as in claim 7, wherein the tetrahydrocurcuminoids is greater than 95% w/w tetrahydrocurcumin.

11. The method as in claim 7, wherein the mammalian skin cells are melanocytes.

12. The method as in claim 7, wherein the mammal is human.

* * * * *